United States Patent [19]

Bird et al.

[11] 4,148,313

[45] Apr. 10, 1979

[54] PATIENT BREATHING MONITORING APPARATUS AND METHOD

[75] Inventors: Forrest M. Bird; Larry S. Martin, both of Palm Springs, Calif.

[73] Assignee: Minnesota Mining and Manufacturing Company, St. Paul, Minn.

[21] Appl. No.: 730,841

[22] Filed: Oct. 8, 1976

[51] Int. Cl.² .............................................. A61M 16/00
[52] U.S. Cl. ...................... 128/145.8; 128/DIG. 17; 128/DIG. 29; 200/82 E; 200/83 L; 200/83 N
[58] Field of Search ............... 128/145.8, 145.6, 145.5, 128/142.2, 25, 2 R, DIG. 29, DIG. 17; 200/82 E, 83 L, 83 N, 83 W, 83 J

[56] References Cited

U.S. PATENT DOCUMENTS

| 2,828,741 | 4/1958 | DeLest ........................ | 128/DIG. 17 |
| 2,972,345 | 2/1961 | Spigel ......................... | 128/DIG. 17 |
| 3,333,584 | 8/1967 | Andreasen et al. .......... | 128/DIG. 29 |
| 3,524,058 | 8/1970 | Robertson et al. .......... | 128/DIG. 29 |
| 3,584,621 | 6/1971 | Bird et al. ................... | 128/145.8 |

FOREIGN PATENT DOCUMENTS

| 973253 | 8/1975 | Canada ........................... | 128/DIG. 29 |
| 1398752 | 6/1975 | United Kingdom ............ | 128/DIG. 29 |

OTHER PUBLICATIONS

Medlock, "Alarm Unit for Use with Intermittent Positive-Pressure Respiration Circuits", Oct. 12, 1957, Lancet, p. 725.

*Primary Examiner*—Henry J. Recla

[57] ABSTRACT

The patient breathing monitoring apparatus is used for monitoring the airway of a patient which has a respirator connected thereto and which is connected to a source of gas. The respirator is of a type which during the inhalation phase supplies inspiratory gases to the airway of the patient and during exhalation phase permits the discharge of gases from the airway of the patient. The monitoring apparatus includes first and second pressure switches each of which has an inlet connected to the airway of the patient. One of the pressure switches is adjustable to sense a decrease in pressure in the airway below a predetermined value whereas the other of the switches is adjustable to sense an increase in pressure in the airway above a predetermined value. An alarm devices is coupled to the pressure switches for giving an alarm when the one switch senses a decrease in pressure below the predetermined value and when the other of the switches senses an increase in pressure above a predetermined value.

5 Claims, 5 Drawing Figures

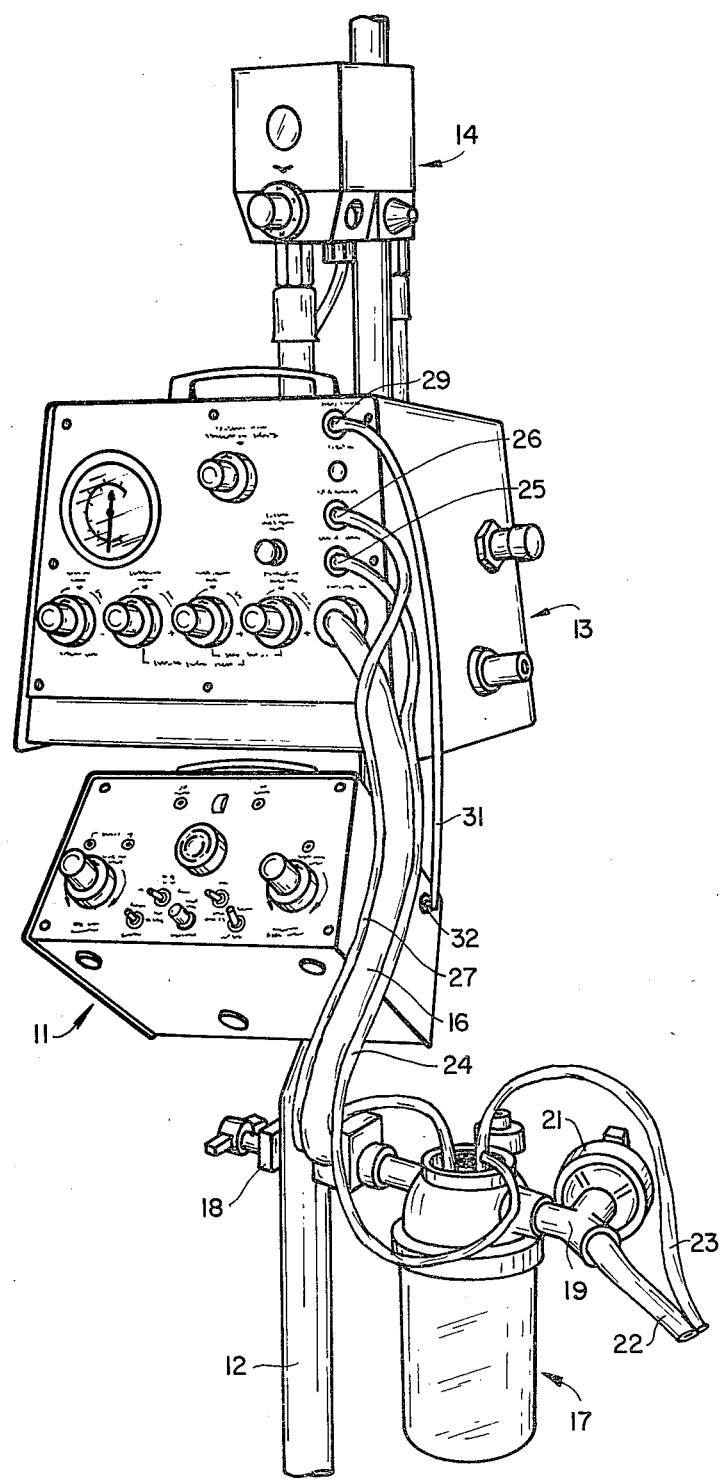
FIG_1

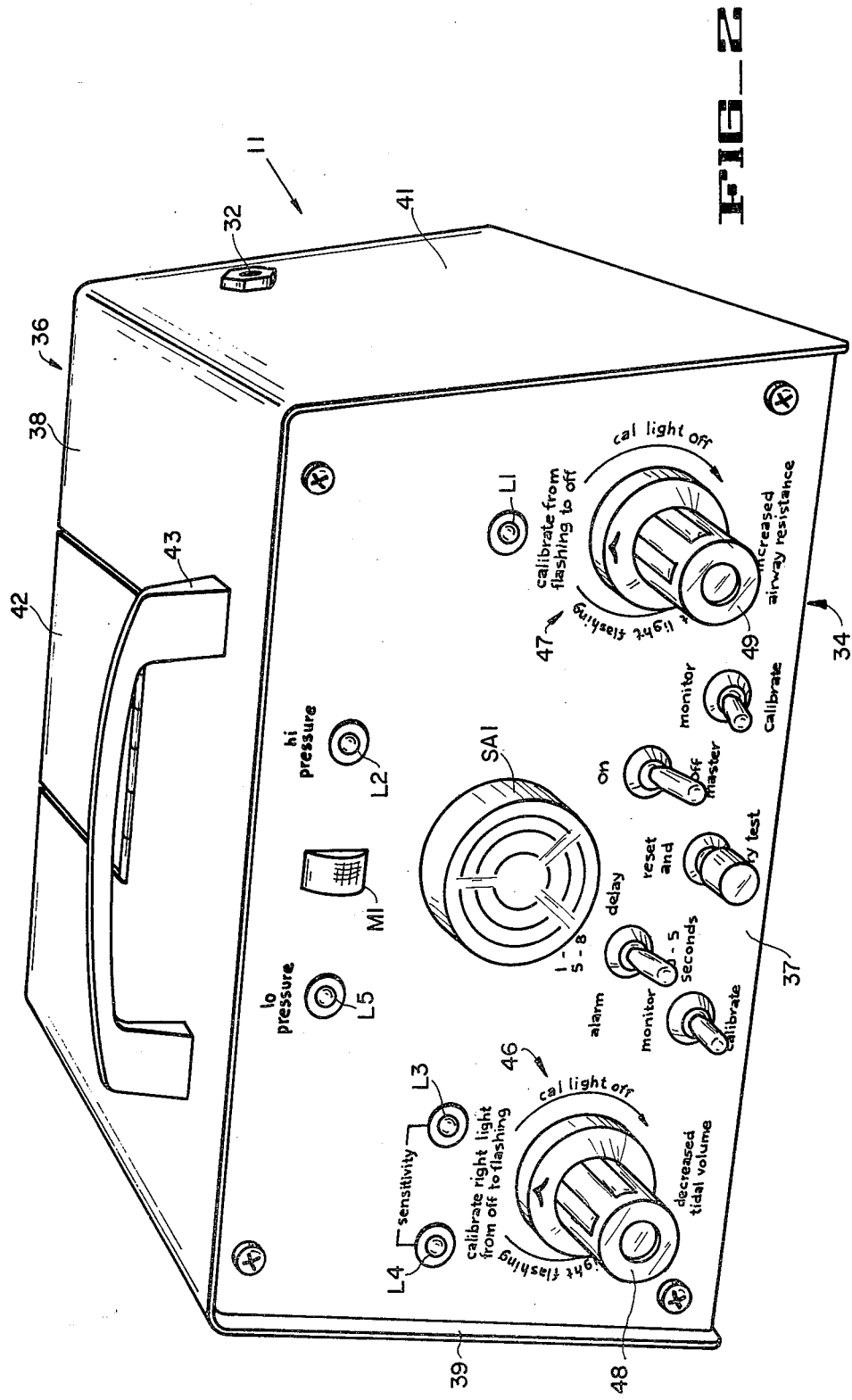

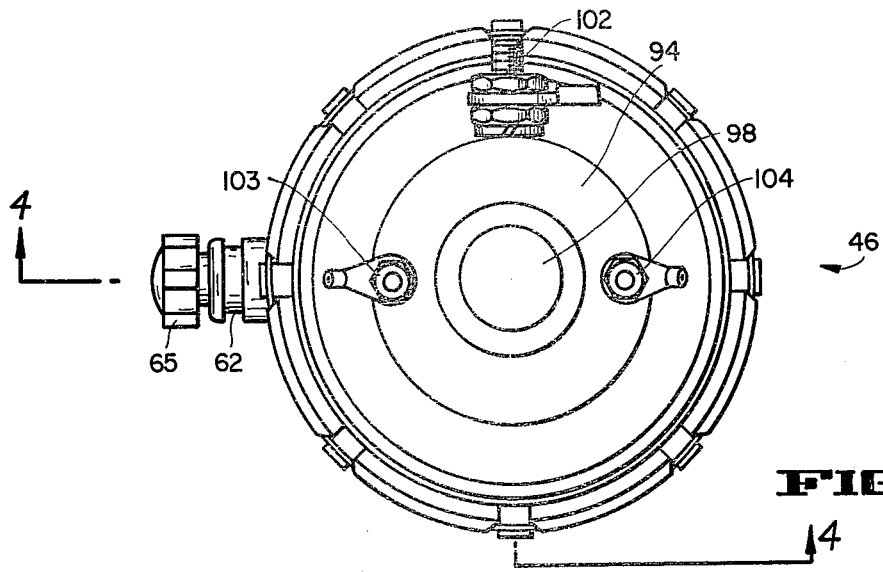
FIG_3
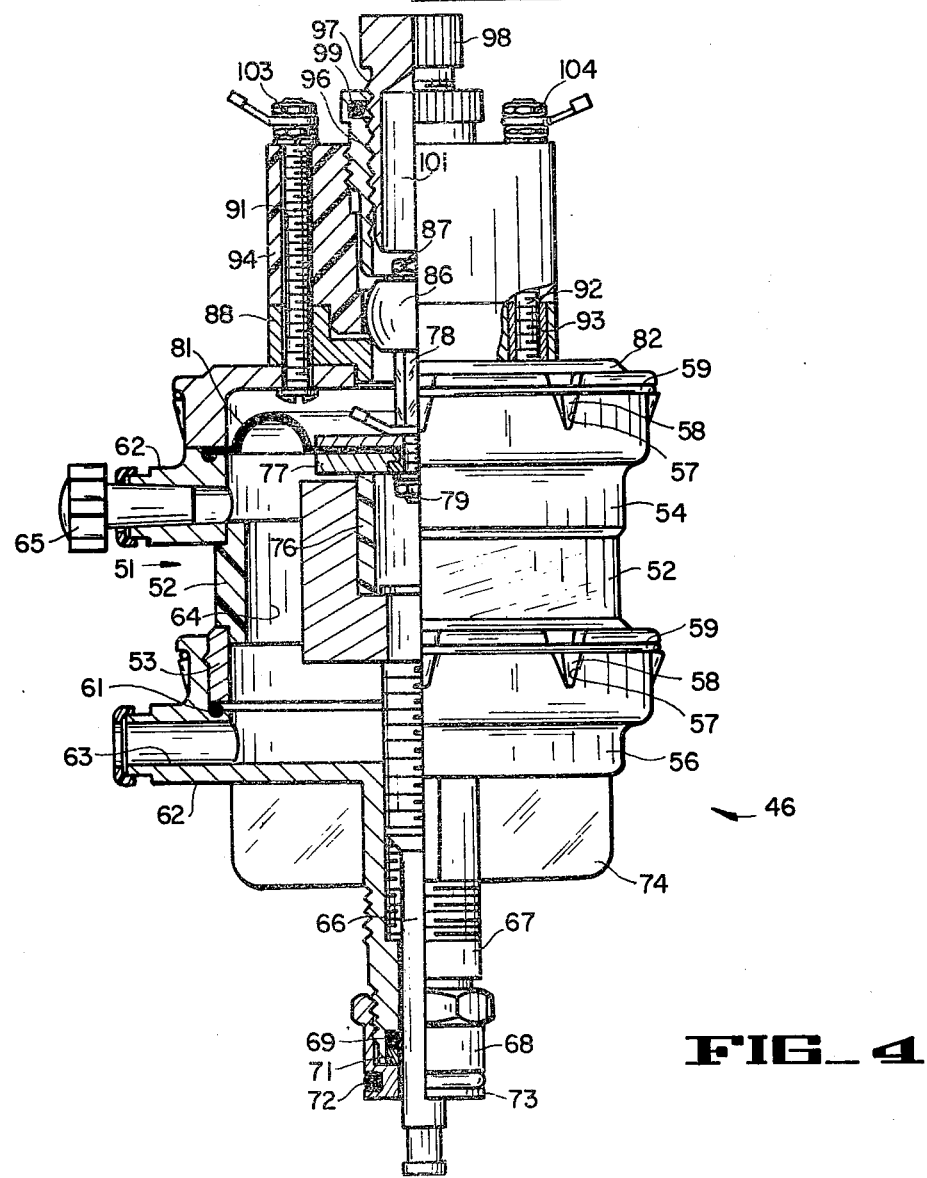
FIG_4

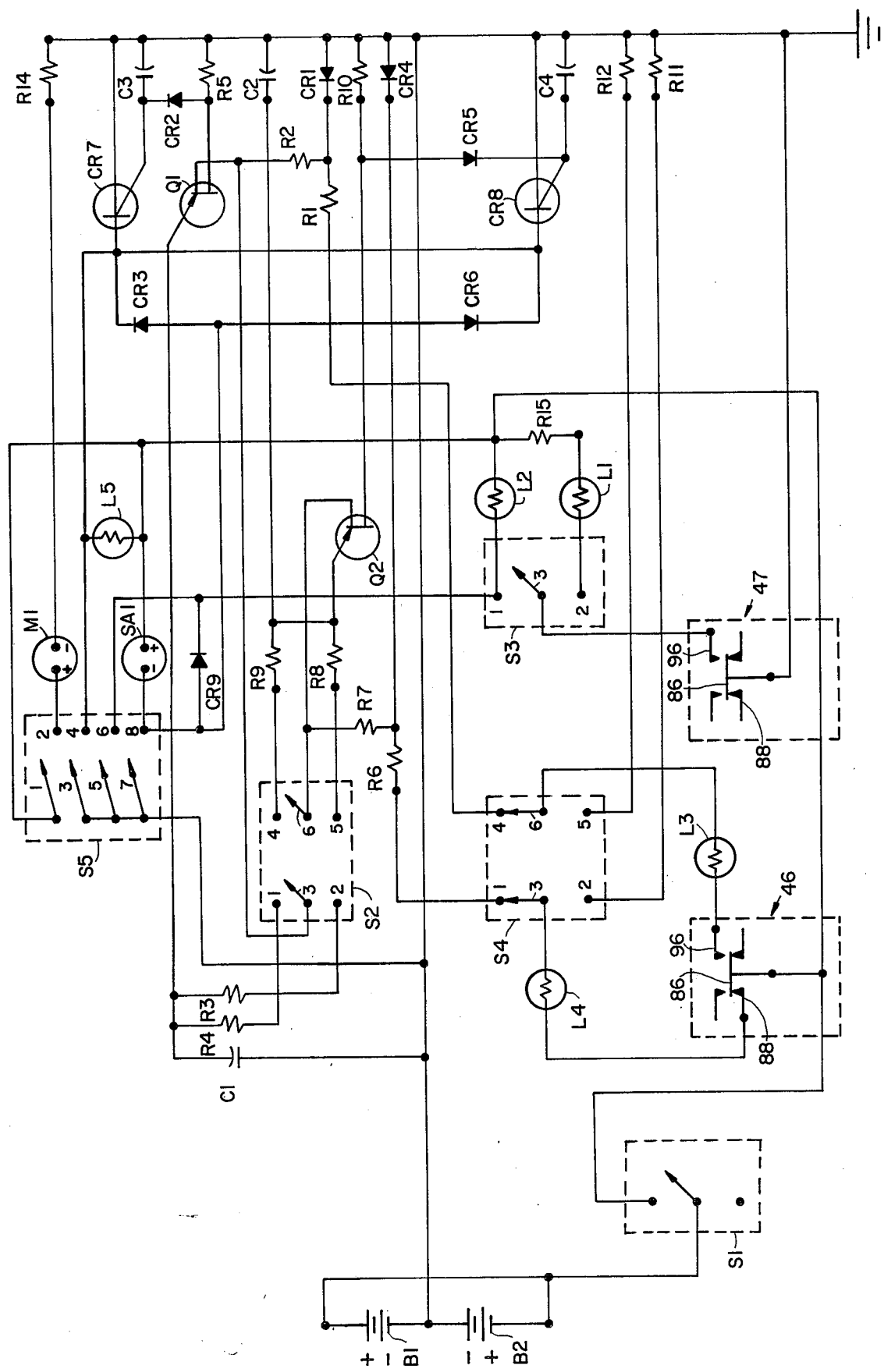
FIG_5

PATIENT BREATHING MONITORING APPARATUS AND METHOD

BACKGROUND OF THE INVENTION

Monitoring devices have heretofore been provided for use with respirators. Many have been inadequate for a number of applications. For example, some would only provide an alarm upon a disconnect. Others which had over pressure alarm capabilities have been found to be unsatisfactory because they were unsuitable for low ranges of pressures which are encountered in intermittent mandatory ventilation and also in neonatal applications. There is therefore a need for a new and improved monitoring apparatus.

SUMMARY OF THE INVENTION AND OBJECTS

The monitoring apparatus is for use in monitoring the patient breathing by monitoring the airway of the patient which has a respirator connected thereto and in which the respirator is connected to a source of gas. The respirator is of a type which has an inhalation phase and an exhalation phase in its operative cycle. During the inhalation phase, it supplies inspiratory gases to the airway of the patient and during the exhalation phase, it permits the discharge of gases from the airway of the patient. The monitoring apparatus includes first and second pressure switches each of which has an inlet connected to the airway of the patient. One of the pressure switches is adjustable to sense a decrease in pressure in the airway of the patient below a predetermined value. The other of the pressure switches is adjustable to sense an increase in pressure in the airway of the patient above a predetermined value. Alarm devices in the form of visual and audible alarms are connected to the pressure switches and are adapted to be actuated by operation of the pressure switches for giving an alarm when pressures above and below the predetermined values are sensed by the pressure switches. The pressure switches are of a type which can be readily calibrated and rapidly move between extreme positions.

In general, it is an object of the present invention to provide a patient breathing monitoring apparatus and method which makes it possible to sense a very low pressure in the airway of the patient.

Another object of the invention is to provide an apparatus and method of the above character in which pressure switches are utilized for sensing the pressure in the patient's airway.

Another object of the invention is to provide an apparatus and method of the above character in which the pressure switches which are utilized more from fully open to fully closed position.

Another object of the invention is to provide an apparatus of the above character which can be readily calibrated.

Another object of the invention is to provide an apparatus of the above character which is relaively low in cost.

Additional objects and features of the invention will appear from the following description in which the preferred embodiment is set forth in detail in conjunction with the accompanying drawing.

DESCRIPTION OF THE DRAWINGS

FIG. 1 is a perspective view of a patient breathing monitoring apparatus incorporating the present invention being utilized with a respirator.

FIG. 2 is an enlarged perspective view of the patient breathing monitoring apparatus shown in FIG. 1.

FIG. 3 is a top plan view of a pressure switch utilized in the patient breathing monitoring apparatus shown in FIG. 2.

FIG. 4 is a cross-sectional view taken along the line 4—4 of FIG. 3.

FIG. 5 is a schematic circuit diagram of the electronic circuitry utilized in the patient breathing monitoring apparatus shown in FIG. 2.

DESCRIPTION OF THE PREFERRED EMBODIMENT

The patient breathing monitoring apparatus 11 is mounted upon a stand 12 of a conventional type. The patient breathing monitoring apparatus is provided with a clamp (not shown) by which it is secured to the stand. The patient breathing monitoring apparatus is adapted to be utilized in conjunction with a respirator 13 which is also mounted upon the stand 12. The respirator 13 is also provided with a bracket (not shown) whereby it can be secured to the stand 12. The respirator 13 is of a conventional pneumatic type such as that described in copending application Ser. No. 605,529, filed Aug. 18, 1975, now U.S. Pat. No. 4,060,078. As described therein, the respirator 13 has an inhalation phase and an exhalation phase in its operative cycle. An oxygen blender 14 is provided for supplying source gas to the respirator or ventilator 13. The blender 14 is of a type described in U.S. Pat. No. 3,727,627. The respirator 13 during the inhalation phase supplies inspiratory gases through a large breathing tube 16 to the inlet of a large nebulizer 17 which is also mounted upon the stand 12 by a bracket 18. The nubulizer 17 is of a type described in U.S. Pat. No. 3,353,536. The output of the nebulizer 17 is connected to a tee 19 that carries a small nebulizer 21 which is of the type described in U.S. Pat. No. 3,172,406. The tee 19 is connected to a large tube 22 which is connected to a patient adapter (not shown) as disclosed in copending application Ser. No. 605,529 filed Aug. 18, 1975. The patient adapter is adapted to be connected to the airway of the patient. An exhalation valve assembly (not shown) is coupled to the patient adapter and includes a valve member movable between open and closed positions. The value member during the inhalation phase is maintained in a closed position by inspiratory gases supplied by a tube 23. The tube 23 is supplied with inspiratory gas from a tube 24 which is connected to the inspiratory power socket 25 provided on the respirator or ventilator 13. The auxiliary nebulization socket 26 is connected by a tube 27 to the nebulizer 17 so that dual jets operate in the nebulizer 17. The ventilator 13 is provided with an airway monitoring socket 29 which is connected to the airway of the patient through the large breathing tubes 16 and 22. The socket 29 is connected by a tube 31 to the inlet socket 32 provided on the patient breathing monitoring apparatus 11.

The patient breathing monitoring apparatus 11 consists of a case which is formed by two U-shaped members 34 and 36. The U-shaped member 34 includes the front panel 37 whereas the U-shaped member 36 includes the top wall 38 and the side walls 39 and 41. The top wall 38 includes a small trap door 42 which is utilized for replacing the batteries utilized in the monitoring apparatus. A handle 43 is secured to the top wall for carrying the monitoring apparatus. The inlet socket 32 is provided on the side wall 41.

The monitoring apparatus 11 includes first and second pressure switches 46 and 47 which are carried by the front panel 37 and which are provided with control knobs 48 and 49 respectively. The pressure switches 46 and 47 are constructed in an identical manner.

The pressure switch 46 is shown in FIGS. 3 and 4 and as shown therein consists of a cylindrical center housing 51. The housing 51 consists of a cylindrical part 52 formed of a suitable material such as a transparent plastic. The ring 53 is secured to one end of the part 52 and an annular cup-shaped member 54 is secured to the other end of the part 52. A cup-shaped member 56 is removably secured to the center housing 51 by suitable cooperative means such as V-shaped slots 57 and V-shaped protrusions 58 which seat in slots 57 and which are retained therein by a retaining ring 59. An O-ring 61 is provided for establishing a good seal between the cup-shaped member 56 and the housing 51. The cup-shaped member 56 is provided with inlet fittings 62 which have inlet passages 63 formed therein which are in communication with a chamber 64 formed in the interior of the cup-shaped member 56 and the housing 51. One of the passages 63 is closed by a plug 65. A shaft 66 is threaded into the cup-shaped member and extends out of a boss 67 formed on the cup-shaped member 56. A packing nut 68 is threaded onto the boss 67 and is provided with sealing means in the form of an O-ring 69 and a washer 71. An O-ring 72 is provided in the annular recess 73 provided in the packing nut 68 and is adapted to be frictionally engaged by a knob 48 mounted upon the shaft 66. The cup-shaped member 56 is provided with upstanding reinforcing ribs 74.

A generally cylindrical magnet 76 is disposed within the central body or housing 51 and is mounted upon the shaft 66 so that as the shaft is rotated, the magnet moves in a direction which is axial of the shaft 66. The magnet 76 is adapted to attract an attraction plate 77. The attraction plate 77 is carried by a hexagonal metal shaft 78 and is retained therein by a nut 79. The attraction plate 77 is on one side of the inner portion of a flexible diaphragm 81, the outer margin of which is clamped between the central housing 51 and a cylindrical member 82 by the use of cooperative mating means of the type hereinbefore described consisting of the V-shaped slots 58 protrusions 59 and a retaining ring 57. The inner portion of the diaphragm 81 is clamped between a retaining plate 83 and the attraction plate 77.

A ball 86 of a conducting material is secured to the shaft 78 and is retained thereon by a nut 87. The ball 86 is adapted to be moved into and out of engagement with an annular conducting contact ring 88. A pair of large screws 91 and 92 extend outwardly from the cylindrical member 82 and extend through the conducting ring 88. The conducting ring 88 is in contact with the screw 91 whereas it is insulated from the screw 92 by means of an insulating sleeve 93. A cylindrical body 94 formed of a suitable material such as plastic is mounted over the annular ring 88 and has the screws 91 and 92 extending therethrough. A sleeve 96 formed of a metal is threaded into the body and carries a carrier screw 97 which is threaded therein. The sleeve 96 also serves as an annular conducting contact ring adapted to be engaged by the movable ball 86. The carrier screw 97 is provided with a knurled knob 98 to facilitate adjustment of the carrier screw. An O-ring 99 is provided to yieldably restrain the movement of the carrier screw 97 within the sleeve 96. A magnet 101 is mounted within the carrier screw 97 and is generally positioned so that it is in axial alignment with the shaft 79 and the ball 86 carried thereby.

An electrical terminal 102 is carried by the cylindrical body 94 which is connected to the sleeve 96 and serves as a normally open contact. Two additional terminals 103 and 104 are provided which are formed on the posts 91 and 92 with the terminal 103 being connected to the conducting ring 88 and terminal 104 being connected to the ball 86.

Operation and use of the pressure switches may now be described in conjunction with the circuitry which is shown in FIG. 5. As can be seen from FIG. 5, the contacts of the pressure switches 46 and 47 have been associated with the corresponding parts as shown in FIGS. 3 and 4. The switches 46 and 47 are shown in the normally closed positions.

As can be seen from FIG. 5, the circuitry includes a pair of batteries B1 and B2, a number of switches S1 through S5, a plurality of light emitting diodes L1 thrugh L5, a plurality of transistors Q1 through Q2, a plurality of resistors R1 through R11, a plurality of capacitors C1 through C4, a plurality of diodes CR1 through CR9, a battery meter m1 and a buzzer SA1.

Operation and use of the circuitry shown in FIG. 5 may now be briefly described as follows. Let it be assumed that the respirator 13 has been connected to a patient and that it is operating and that it is desied to utilize the patient breathing monitoring apparatus 11 in conjunction therewith. The pressure being monitored is being supplied to the pressure switches 46 and 47. Let it be assumed that the resirator 13 has been set for the desired flows and volumes for the patient as for example at a peak pressure of 20 cm. This pressure of 20 cm. will be supplied to the two switches 46 and 47 as hereinbefore described. Let it be assumed that the patient breathing monitoring apparatus 11 is out of adjustment and that it is now desired to adjust the same in conjunction with the pressure of the gases being supplied to the patient. The master on-off power switch S1 is moved to the closed position and then the monitor calibrate switches S3 and S4 are held in a depressed condition to prevent false alarming.

As soon as the power switch S1 is closed, power is supplied to the movable contact 86 of the pressure switch 46. The power is also supplied to the voltage dropping resistor R15 to one side of the light emitting diode L1. Power is also supplied to one side of the low pressure indicating light emitting diode L5 and to one side of the buzzer SA1.

Now let it be assumed that the monitor calibrate switch S4 is moved from the normally closed position in which the movable contacts 3 and 6 are engaged with the contacts 1 and 4 to the normally open position in which the movable contacts 3 and 6 are in engagement with the contacts 2 and 5. The contact knob 48 of the pressure switch 46 is moved in a clockwise direction which moves the magnet 76 closer to the attraction plate 77. This is continued until the force of the magnet overcomes the pressure in the chamber 64 against the diaphragm 81 and permits the ball 86 to move in contact with the ring 88. This interrupts the flow of power through the light emitting diode L3, the circuit for which is closed to ground through the contacts 5 and 6 of the switch S4 through a resistor R12 to ground. Thus the light L3 is no longer energized. At the same time that the light L3 is deenergized, light L4 is energized by power being supplied through the movable contact of the pressure switch 46 through the normally closed contact 88 and then through the light L4 through the movable contact 3 and contact 2 of the switch S4 through the resistor R11 to ground.

As soon as this condition has been created with the light L3 off and light L4 on, the control knob 48 is moved in a counterclockwise direction until the peak pressure being sensed in the patient airway and being supplied to the diaphragm 81 is sufficient to overcome the attraction of the magnet 76 to the attraction plate 77. As soon as this occurs, the pressure switch 46 will when the peak pressure is encountered move to the normally open position and the light L3 will flash on. Because the peak pressure is only occurring periodically in the patient airway, the light L3 will flash on only when the peak pressure is encountered and then will go off when the peak pressure condition passes and will not go on until another peak pressure is encountered.

As soon as the pressure switch 46 has been adjusted so that the light L3 has just begun to flash on and off, the calibrate monitor switch S4 can be released so that the contacts 3 and 6 move back to the normally closed positions. Power will then be supplied from the movable contact 86 through the normally open contact 96 through the light L3 through the movable contact 6, and contact 4 of switch S4 through the isolating resistor R1 and through the zener diode CR1 to ground. The zener diode is utilized for clamping off the voltage at a suitable voltage such as 6.2 volts so that a drop in the voltage supplied by the battery B2 will not affect the operation of the circuit. Power is also supplied through another isolation resistor R2 to a unijunction transistor Q1. Power is also supplied to the movable contact 3 of the timing switch S2. When the movable contact 3 of the switch S2 is in contact with contact 1, it is connected to a resistor R4 and through a capacitor C1 to ground. When the movable contact 3 is in contact with the contact 2, it is connected to the resistor R3 through C1 to ground. the values of the resistors R3 and R4 have been chosen to provide two different time constants as for example five or three seconds for the inspiratory phase. The capacitor C1 is charged with the voltage through either the resistor R3 or R4 depending upon the position of the switch s2 and when it reaches a certain charge as for example four volts, it triggers the unijunction transistor Q1 which sends a gate signal through the isolation diode CR2 and then through the SCR device CR7 which applies a ground to the audio alarm SA1 and the light emitting diode L5.

The CR7 device also applies a ground through the isolating diode CR3 to one side of the alarm device SA1. The other sides of the alarm device SA1 and the light L5 are connected to the battery B2 through the switch S1. Thus an alarm is caused to be sounded and a light to be lit when the inspiratory phase of the peak pressure occurs for too long a time. The resistor R5 and the capacitor C3 are provided for spike suppression and insure that the alarm SA1 is not prematurely energized. The isolation diode CR2 insures that erroneous signals from other parts of the circuit will not trigger the alarm SA1.

During the expiratory phase or exhalation phase of the ventilator, the pressure switch 46 will be in the normally closed position and power will be supplied from the movable contact 86 through the contact 88 through the light L4 through the movable contact 3 to contact 1 of switch S4 and then through the isolation resistor R6 and through the zener dioe CR4 to ground. Voltage is also supplied from the resistor R6 to isolation resistor R7 to the unijunction transistor Q2. Voltage is also supplied from the resistor R7 to the movable contact 6 of the selector switch S2 which provides two different times either eight seconds when the movable contact 6 is in contact with the contact 4 which is connected through a resistor R9 and a capacitor C2 to ground or five seconds when the movable contact 6 is in contact with the contact 5 which is connected through the resistor R8 and capacitor C2 to ground. Thus, as in conjunction with the resistors R3 and R4 and C1, when the voltage on capacitor C2 reaches approximately four volts, a trigger signal will be supplied from the transistor Q2 through the isolation diode CR5 to the SCR CR8 to trigger it to cause it to apply a ground to one side of the light L5 and also to apply a ground through the isolation diode CR6 to one side of the alarm SA1. Thus, it can be seen that the unijunction transistor Q2 performs two functions just as the unijunction transistor Q1 did. When the transistor Q2 is triggered, the low pressure alarm light L5 is lit and the alarm SA1 is sounded. As hereinafter explained more in detail, it can be seen that the pressure switch 46 will monitor a lower pressure condition either in the inspiratory or expiratory phase of the respirator.

Let it be assumed that it now desired to calibrate the pressure conditions to be sensed by the pressure switch 47. With the switch S3 in the calibrate position with movable contact 3 in contact with the terminal 2, voltage is supplied from the on/off power switch S1 through the isolation resistor R15 through the light emitting diode L1 through contact 2 and movable contact 3 through the normally open contact 96 to the movable contact 86 of the pressure switch 47 to ground to energize the light L1. What is desired at this stage of the calibration, is to obtain flashing of the light L1. This is accomplished by rotating the knob 45 in a clockwise direction. This decreases the spacing between the magnet 76 and the attraction plate 77 until the magnetic force becomes sufficient to overcome the pressure of the patient in the chamber 70. The pressure switch 47 will then remain in a normally closed position until there is a rise in pressure in the airway of the patient which will cause the pressure switch to move to a normally closed position to light L1 for the duration of the over pressure condition. As soon as the light L1 is flashing the knob 49 is rotated counterclockwise to move the magnet 76 away from the attraction plate 77 sufficiently far so that during the inhalation and exhalation phases, the pressure switch 47 will remain in a normally open position and so that the light L1 will remain off. As soon as this has been accomplished, the monitor calibrate switch S3 can be released so that the movable contact 3 will come into contact with the contact 1. When an over pressure condition is then sensed by the pressure switch 47 and it is moved from the normally closed to a normally open position, power is supplied from the switch S1 to the light emitting diode L2 through the contacts 1 and 3 of the switch S3 and through the contacts 96 and 86 of the pressure switch 47 to ground to energize the light L2. Power is also supplied from the terminal 1 of the switch S3 through an isolation diode CR9 to the negative side of the sound alarm SA-1.

The capacitor C4 and the resistor R10 perform the same spike suppression functions as the capacitor C3 and the resistor R5.

A press to test switch S5 is provided. Power is supplied to the movable contact 1 of the switch from the power switch S1 to the contact to one side of the meter M1. The other side of the meter M1 is connected to ground through the resistor R14. The resistor R14 provides approximately a 2½ volt drop. This voltage drop is proportional to the voltage being supplied to the battery and can be utilized to ascertain when the batteries should be replaced.

From the foregoing description, it can be seen that the patient breathing monitoring apparatus can be readily calibrated by following relatively simple instructions for sensing low pressure conditions and also high pressure conditions in the inhalation and exhalation phases. This can be accomplished merely by rotating two knobs and watching certain lights as hereinbefore described. The monitor also can be readily adjusted to operate for adults and infants by use of the selector switch S2 which in the upper position selects a timing suitable for adults and in the lower position selects a timing suitable for infants.

It has been found that the patient breathing monitoring apparatus is particularly efficacious because of the use of the pressure switches 46 and 47 which because of their construction are either fully open or fully closed. There is no backlash as would be created by a spring which would create a greater pressure the further the valve is open. For this reason the monitoring apparatus is capable of monitoring very low pressures. In addition, it is capable of monitoring patients with respirators which are supplying only intermittent mandatory ventilation. In such cases, the pressures to be sensed may be as low as those corresponding to 3 to 4 cm. of water. With the present monitoring apparatus, it has been found that it is possible to sense pressures as low as one fourth of a cm. of water.

It is apparent that under pressure and over pressure conditions can be readily sensed by the patient breathing monitoring apparatus. For example, a disconnect would be immediately sensed by the pressure switch 46 because it would immediately indicate very low pressure or no pressure. Over pressure conditions also can be readily sensed by the pressure switch 47. Since the patient monitoring apparatus is actually monitoring the pressure in the patient airway, the apparatus will also give an alarm when the patient stops breathing.

Thus, it can be seen that the patient breathing monitoring apparatus monitors pressure rise and pressure drop and disconnects. It also can be utilized for monitoring small infants and large adults when the patient is breathing spontaneously or if the patient stops breathing. Although the patient breathing monitoring apparatus has been shown for use with a particular respirator or ventilator, it should be appreciated that the patient breathing monitoring apparatus can be used universally with all types of respirators. All that is required is a tube from the patient breathing monitoring apparatus which can be connected to the airway of the patient to monitor the pressures in the patient airway.

What is claimed is:

1. In a patient breathing monitoring apparatus for use with a respirator connected to a source of gas and having a breathing outlet connected to the airway of a patient for supplying inspiratory gases to the airway of the patient during the inspiratory phase and permitting discharge of gases from the airway of the patient during the expiratory phase, the monitoring apparatus comprising first and second pressure switches adapted to be placed in communication with the breathing outlet, one of said switches including means adjustable to sense a decrease in pressure in the breathing tube outlet below a predetermined value and the other of said switches including means adjustable to sense a decrease in pressure in the breathing tube outlet below a predetermined value and the other of said switches including means adjustable to sense an increase in pressure in the breathing tube outlet above a predetermined value, means coupled to the pressure switches for giving an alarm when the switches sense pressures above or below the predetermined values and means for calibrating the pressure switches including lights and circuitry connecting the lights to the pressure switches so that the light for the pressure switch for sensing a pressure below a predetermined value can be adjusted from off to flashing to calibrate the same and so that the light for the pressure switch for sensing a pressure above a predetermined value can be calibrated from flashing to off to calibrate the same.

2. In a patient breathing monitoring apparatus for use with a respirator connected to a source of gas and having a breathing outlet connected to the airway of a patient for supplying inspiratory gases to the airway of the patient during the inspiratory phase and permitting discharge of gases from the airway of the patient during the expiratory phase, the monitoring apparatus comprising an inlet adapted to be placed in communication with the breathing outlet, first and second pressure switches in communication with the inlet, one of said switches including means adjustable to sense a decrease in the breathing tube outlet below a predetermined value and the other of said switches including means adjustable to sense an increase in pressure in the breathing tube outlet above a predetermined value, each of said pressure switches includes a housing, a diaphragm mounted within the housing and in cooperation with the housing forming a first chamber in the housing on one side of the diaphragm in communication with said inlet, cooperative magnetic means disposed within the housing and having one part thereof mounted to the diaphragm and having another part adjustably positioned within the housing, electrical contact means mounted to the diaphragm and movable with the diaphragm so that in one position of the diaphragm, one contact condition is created and in another position of the diaphragm, a different contact condition is created and switch means for deactivating the alarm means for all ranges of pressure during the time the pressure switches are being calibrated to provide alarms above and below the predetermined values.

3. In a patient breathing monitoring apparatus for use with a respirator connected to a source of gas and having a breathing outlet connected to the airway of a patient for supplying inspiratory gases to the airway of the patient during the inspiratory phase and permitting discharge of gases from the airway of the patient during the expiratory phase, the monitoring apparatus comprising an inlet adapted to be placed in communication with the breathing outlet, first and second pressure switches in communication with the inlet, one of said switches including means adjustable to sense a decrease in pressure in the breathing tube outlet below a predetermined value and the other of said switches including means adjustable to sense an increase in pressure in the breathing tube outlet above a predetermined value each of said pressure switches includes a housing, a diaphragm mounted within the housing and in cooperation with the housing forming a first chamber in the housing on one side of the diaphragm in communication with said inlet, cooperative magnetic means disposed within the housing and having one part thereof mounted to the diaphragm and having another part adjustably positioned within the housing, electrical contact means mounted to the diaphragm and movable with the diaphragm so that in one position of the diaphragm, one contact condition is created and in another position of the diaphragm, a different contact condition is created and meas for providing an alarm when the inspiratory phase lasts beyond a predetermined time.

4. Apparatus as in claim 3 wherein said means for giving an alarm when the inspiratory phase lasts beyond a predetermined time includes means for selecting at least two different times, one of the times being suitable for adults and the other time being suitable for infants.

5. In a patient breathing monitoring apparatus for use with a respirator connected to a source of gas and having a breathing outlet connected to the airway of a patient during the inspiratory phase and permitting discharge of gases from the airway of the patient during the expiratory phase, the monitoring apparatus comprising an inlet adapted to be placed in communication with the breathing outlet, first and second pressure switches in communication with the inlet, one of said switches including means adjustable to sense a decrease in pressure in the breathing tube outlet below a predetermined value and the other of said switches including means adjustable to sense an increase in pressure in the breathing tube outlet above a predetermined value, each of said pressure switches includes a housing, a diaphragm mounted within the housing and in cooperation with the housing forming a first chamber in the housing on one side of the diaphragm in communication with said inlet, cooperative magnetic means disposed within the housing and having one part thereof mounted to the diaphragm and having another part adjustably positioned within the housing, electrical contact means mounted to the diaphragm and movable with the diaphragm so that in one position of the diaphragm, one contact condition is created and in another position of the diaphragm, a different contact condition is created and means for calibrating the pressure switches including lights and circuitry connecting the lights to the pressure switches so that the light from one of the pressure switches can be adjusted from off to flashing to calibrate the same and so that the light for the other of the pressure switches can be adjusted from flashing to off to calibrate the same.

* * * * *